United States Patent [19]
Comben et al.

[11] Patent Number: 5,354,326
[45] Date of Patent: Oct. 11, 1994

[54] SCREENING CABLE CONNECTOR FOR INTERFACE TO IMPLANTED LEAD

[75] Inventors: Richard H. Comben, St. Paul, Minn.; Barry J. Grant, Roberts, Wis.; Michael D. Serfling, St. Louis Park, Minn.; Thomas E. Cross, Jr., St. Francis, Minn.; David J. Stanton, Anoka, Minn.

[73] Assignee: Medtronic, Inc., Minneapolis, Minn.

[21] Appl. No.: 9,607

[22] Filed: Jan. 27, 1993

[51] Int. Cl.$^5$ .................................. A61N 1/02
[52] U.S. Cl. .................... 607/115; 128/642; 439/299; 439/342
[58] Field of Search ............. 128/642; 607/115, 116, 607/119, 122; 439/296, 299, 308, 312, 314, 316, 317, 318, 342, 338, 376, 262, 265, 668, 669

[56] References Cited

U.S. PATENT DOCUMENTS

| | | | |
|---|---|---|---|
| 3,222,471 | 12/1965 | Steinkamp | 439/669 |
| 3,287,031 | 9/1964 | Simmons et al. | 439/376 |
| 3,478,302 | 11/1969 | Chirumbolo | 439/314 |
| 3,551,880 | 12/1970 | Hartwell | 439/314 |
| 4,074,927 | 2/1978 | Bail | 339/89 |
| 4,165,911 | 8/1979 | Laudig | 439/314 |
| 4,166,465 | 9/1979 | Esty et al. | 128/303 |
| 4,744,370 | 5/1988 | Harris . | |
| 4,796,615 | 1/1989 | Bullock et al. | 128/202.27 |
| 4,797,125 | 1/1989 | Malana | 439/729 |
| 4,850,359 | 7/1989 | Putz | 128/642 |
| 4,940,424 | 7/1990 | Odbert | 439/314 X |
| 4,960,395 | 10/1990 | Ushler | 439/864 |
| 5,082,453 | 1/1992 | Stutz, Jr. | 439/265 |

Primary Examiner—Lee S. Cohen
Assistant Examiner—Jeffrey R. Jastrzab
Attorney, Agent, or Firm—Terry L. Wiles; Harold R. Patton

[57] ABSTRACT

A connector for establishing an external connection with multiple-conductor implantable leads. The connector body is generally cylindrical in shape and includes a unique twist lock design. The cylindrical connector body has two sections which rotate axially with respect to one another, from an 'open' position to a 'closed' position. Each of the sections has a longitudinal slot therein extending along its surface parallel to the cylindrical axis of the connector. In the 'open' position, the slots in the respective sections are in alignment, forming a single longitudinal opening. The opening is keyed to accept an elongated end piece from a lead stylet, the end piece being attached to the end of the implantable electrode. The end piece supports the end of the lead such that the multiple, spaced apart electrical contacts disposed on the lead are exposed on at least one side. The cylindrical body has similarly spaced apart contacts disposed therein, such that when the stylet end piece is placed into the longitudinal opening in the connector, the contacts on the supported lead are brought into contact with the corresponding contacts disposed within the connector body. The end piece is secured inside the connector body by twisting the sections of the connector body into their 'closed' position, so that the respective sets of spaced apart contacts are held in firm contact with each other. As the sections of the cylindrical connector body are twisted into the 'closed' position, a downward pressure is exerted mechanically on the end piece to ensure good electrical contact.

5 Claims, 7 Drawing Sheets

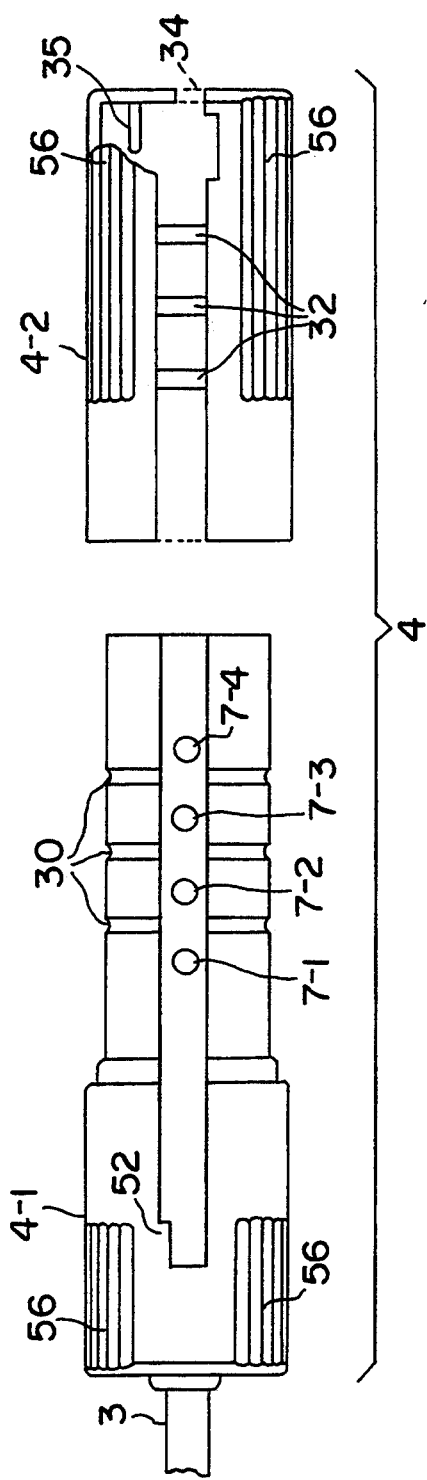
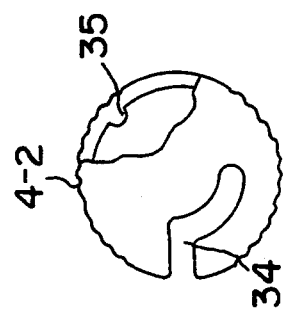
FIG.4b
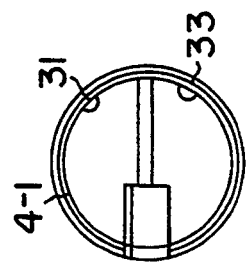
FIG.4a
FIG.3

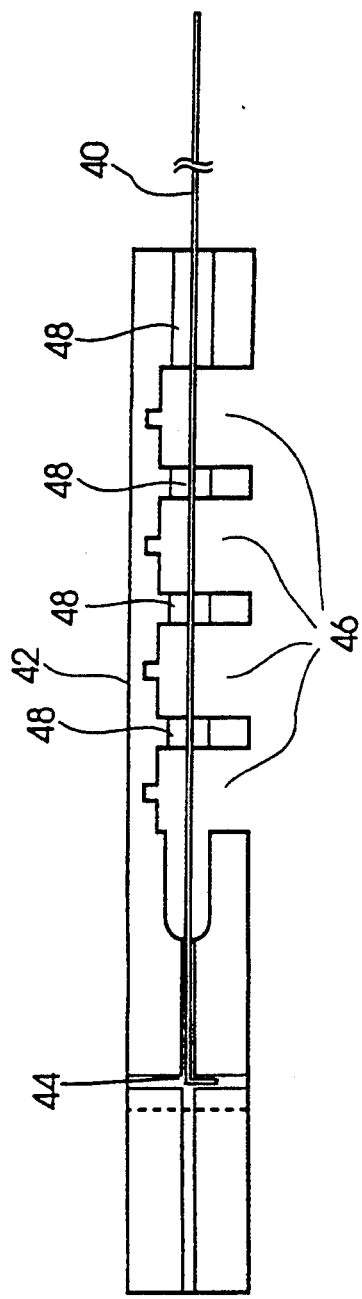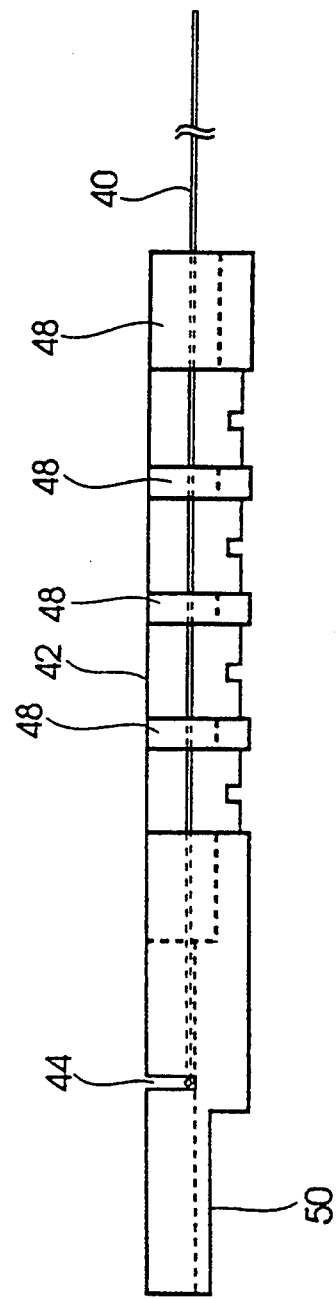

SCREENING CABLE CONNECTOR FOR INTERFACE TO IMPLANTED LEAD

FIELD OF THE INVENTION

This invention relates to the field of implantable medical devices, and more particularly relates to a multiple-conductor cable connector for use in conjunction with implantable sensing and or stimulating leads.

BACKGROUND OF THE INVENTION

The state of the art of implantable pulse generators for stimulating human tissue has advanced to the point that such devices are being designed and used in increasing numbers to treat a wide variety of medical conditions. In addition to implantable pulse generators for treating many different types of cardiac conditions (bradycardia, tachycardia, fibrillation, and the like), so-called neurological pulse generators have been provided for stimulating a patient's nervous system, in order to treat such diverse conditions as pain, motor impairment, incontinence, and impotence, to name only a few.

In most cases, electrical stimulating pulses are conveyed from an implanted pulse generator to the desired stimulation site by means of an implanted lead having exposed electrodes at its distal end. The proximal end of the lead is coupled to the pulse generator by one of many known types of connector mechanisms, after the distal end of the lead has been placed in the desired position in the patient.

In order to achieve the desired effects from delivery of stimulating pulses from an implantable pulse generator, it is of course very important that the lead be properly positioned in the patient, so that as much of the stimulating energy as possible is delivered to the appropriate site. While this is true for all kinds of stimulating pulse therapies, lead positioning is especially critical in the area of neurological stimulation, such as when stimulating pulses are delivered by a lead positioned in the epidural space adjoining the patient's spinal column. The delicate and highly sensitive nature of the spinal column, and the possible harmful or otherwise undesirable effects of delivering stimulating pulses to an inappropriate site in this area, accentuates the need for precise lead placement in such cases.

In order to determine and/or verify the proper placement of a neurological stimulating lead in a patient, a so-called 'screening' procedure is often carried out in conjunction with the implantation of the lead. During the screening procedure, the lead may be initially and temporarily connected to an external device capable of simulating the operation of the pulse generator to be implanted. One such external device is the Model 3625 Neurological Screener available from Medtronic, Inc., Minneapolis, Minn. With an external device such as the 3625 Screener coupled to the lead, the effects of the stimulating pulses can be observed and placement of the lead can be adjusted to achieve optimal results, prior to fully completing the implantation of the pulse generator.

Typically, the proximal, or connector, end of the implantable lead is adapted to be connected to the implantable pulse generator. As a result, the connector end is preferably designed to be as compact as possible, and is usually not designed to be conveniently coupled to anything but the implantable pulse generator. Thus, in the prior art, temporarily coupling the connector end of the lead to a screening device or other external accessory often involves an expensive connector block similar to that normally found on the implanted device. Alternatively, "alligator" clips or the like may be used.

The present invention relates to a connector designed to connect implantable leads to an external cable during and/or following implantation of the lead, in order to facilitate trial sensing or stimulation, electrode positioning, and patient response prior to the more permanent connection of the lead to an implantable pulse generator or the like.

SUMMARY OF THE INVENTION

In accordance with the present invention, a connector is provided for establishing an external connection with multiple-conductor implantable leads. The connector body is generally cylindrical in shape and includes a unique twist lock design. The cylindrical connector body has two sections which rotate axially with respect to one another, from an 'open' position to a 'closed' position. Each of the sections has a longitudinal slot therein extending along its surface parallel to the cylindrical axis of the connector. In the 'open' position, the slots in the respective sections are in alignment, forming a single longitudinal opening. The opening is keyed to accept an elongated end piece from a lead stylet, the end piece being attached to the end of the implantable electrode. The end piece supports the end of the lead such that the multiple, spaced apart electrical contacts disposed on the lead are exposed on at least one side. The cylindrical body has similarly spaced apart contacts disposed therein, such that when the stylet end piece is placed into the longitudinal opening in the connector, the contacts on the supported lead are brought into contact with the corresponding contacts disposed within the connector body. The end piece is secured inside the connector body by twisting the sections of the connector body into their 'closed' position, so that the respective sets of spaced apart contacts are held in firm contact with each other. As the sections of the cylindrical connector body are twisted into the 'closed' position, a downward pressure is exerted mechanically on the end piece to ensure good electrical contact. A detent means is included to releasably lock the sections in either the 'open' or 'closed' positions.

The connector of the present invention offers several advantages over the prior art methods known to the inventors. One advantage is that the connector is simple to use, which is particularly advantageous in a surgical setting. Another advantage is that the connector in accordance with the present invention is small, inexpensive and lightweight, yet provides a faultless and sure connection to the multiple conductors in the lead.

BRIEF DESCRIPTION OF THE DRAWINGS

The foregoing and other aspects of the present invention will be best appreciated with reference to the detailed description of a specific embodiment of the invention, which follows, when read in conjunction with the accompanying drawings, wherein:

FIG. 3 is an enlarged, exploded view of the connector from FIGS. 1 and 2;

FIGS. 4a and 4b are end views of the connector halves of the connector from FIGS. 1 through 3;

FIGS. 6a and 6b are top and side views, respectively, of a stylet and end piece for adapting the lead of FIG. 5 to be coupled to the connector of FIGS. 1 through 3;

DETAILED DESCRIPTION OF A SPECIFIC EMBODIMENT OF THE INVENTION

Figure 1:
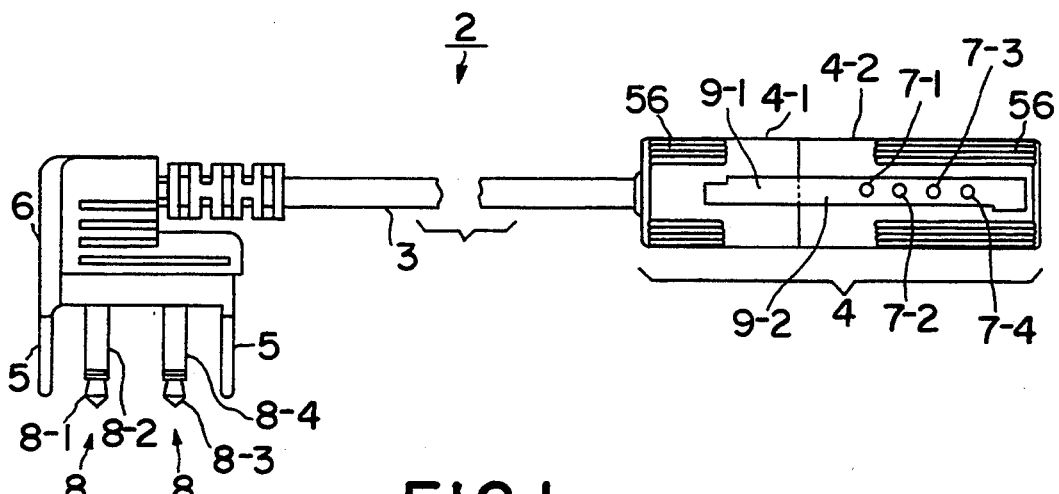
FIG. 1 is an illustration of a screening cable having a connector in accordance with one embodiment of the present invention.

In FIG. 1, there is shown a screening cable 2 having a connector 4 in accordance with one embodiment of the present invention thereon. At one end of cable 2, a two-pronged plug 6 is provided for coupling cable 2 to an external lead implant accessory, which may be, for example, a Medtronic Model 3625 Neurological Screener, commercially available from Medtronic, Inc., Minneapolis, Minn.

Two-pronged plug 6 includes two conventional ⅛-inch male "stereo" pins 8, providing for four separate contact points 8-1, 8-2, 8-3, and 8-4, as would be apparent to those of ordinary skill in the art. Although the present invention will be described herein with reference to cable 2 having four conductors therein, it is to be understood that the present invention may be advantageously employed in situations having more or fewer conductors, as necessary in a given application, and it is believed that the manner of adapting the present invention to such situations would be obvious to those of ordinary skill in the art having the benefit of the present disclosure.

Two-pronged plug 6 may be provided, as shown in FIG. 1, with "wings" 5 disposed alongside pins 8, where wings 5 serve as a safety precaution so that plug 6 may not mistakenly be plugged into an electrical outlet or the like.

With continued reference to FIG. 1, plug 6 is coupled, via a four-conductor cable 3, to cylindrical connector body 4 in accordance with the presently disclosed embodiment of the invention. Connector body 4 comprises two partially nested cylindrical halves, 4-1 and 4-2, with half 4-2 being rotatable with respect to half 4-1, as will be hereinafter described in greater detail. Connector body 4 has a longitudinal slot therein, with a first portion 9-1 of the slot being located in connector half 4-1, and a second portion 9-2 of the slot being located in connector half 4-2. In an 'open' position as is depicted in FIG. 1, the respective slots 9-1 and 9-2 in halves 4-1 and 4-2 are aligned to effectively form a single slot.

Figure 2:
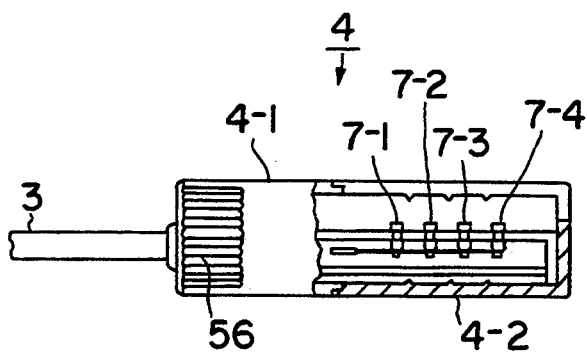
FIG. 2 is a partially cut-away side view of the connector of FIG. 1.

Connector body 4 has, in the presently disclosed embodiment, four spaced apart electrical contacts 7-1, 7-2, 7-3, and 7-4 disposed therein, these contacts being exposed on the bottom of slot 9-2 when connector 4 is in its 'open' position. Each one of contacts 7-1, 7-2, 7-3, and 7-4 is electrically coupled via one of four separate conductors in cable 3 to a respective one of contact points 8-1, 8-2, 8-3, and 8-4. In FIG. 2, a partially cut-away side view of connector body 4 is shown, in order to further illustrate how contacts 7-1, 7-2, 7-3, and 7-4 are disposed within connector 4.

In FIG. 3, a greatly enlarged, exploded view of connector 4 is shown. It is to be understood that connector halves 4-1 and 4-2 are never separated during operation, this being shown in FIG. 3 solely for the purposes of describing the presently disclosed embodiment of the invention. Connector 4 is preferably made of compression-molded plastic or the like, in accordance with common practice in the art. As can be seen from FIG. 3, connector half 4-1 is provided with a series of circumferential grooves 30 disposed therearound. Connector half 4-2 is provided with a corresponding series of circumferential ridges 32 disposed on its inner surface. As would be appreciated by those of ordinary skill in the art, when connector halves 4-1 and 4-2 are assembled as shown in FIGS. 1 and 2, ridges 32 are engaged in grooves 30, thereby axially securing connector halves 4-1 and 4-2. This interlocking of halves 4-1 and 4-2 permits connector half 4-2 to be twisted around the common axis of halves 4-1 and 4-2, while preventing halves 4-1 and 4-2 from being axially pulled apart.

FIGS. 4a and 4b are end views of connector halves 4-1 and 4-2, respectively. At least two longitudinal grooves, 31 and 33, are formed in the surface of connector half 4-1. Longitudinal grooves 31 and 33 are spaced at approximately 90 degrees from one another with respect to the cylindrical axis of the connector. Raised portion 35 located on the inner surface of connector half 4-2 is shaped to be accommodated by grooves 31 and 33 as the connectors halves are rotated with respect to one another. When the connector halves are rotated so that raised portion 35 mates with groove 31 the connector is releasably locked in the 'open' position. When the connector halves are rotated so that raised portion 35 mates with detent 33 the connector is releasably locked in the 'closed' position. Longitudinal grooves 31 and 33 together with raised portion 35 comprise a locking means which provides the user with audible and tactile feedback to confirm that the connector is in the full 'open' or 'closed' position.

With further reference to FIG. 4b a bayonet-type groove 34 is shown cut into the end of connector half 4-2. Groove 34 permits the end of a lead to be disposed in slots 9-1 and 9-2, as will be hereinafter described in greater detail with reference to later figures.

Figure 5:
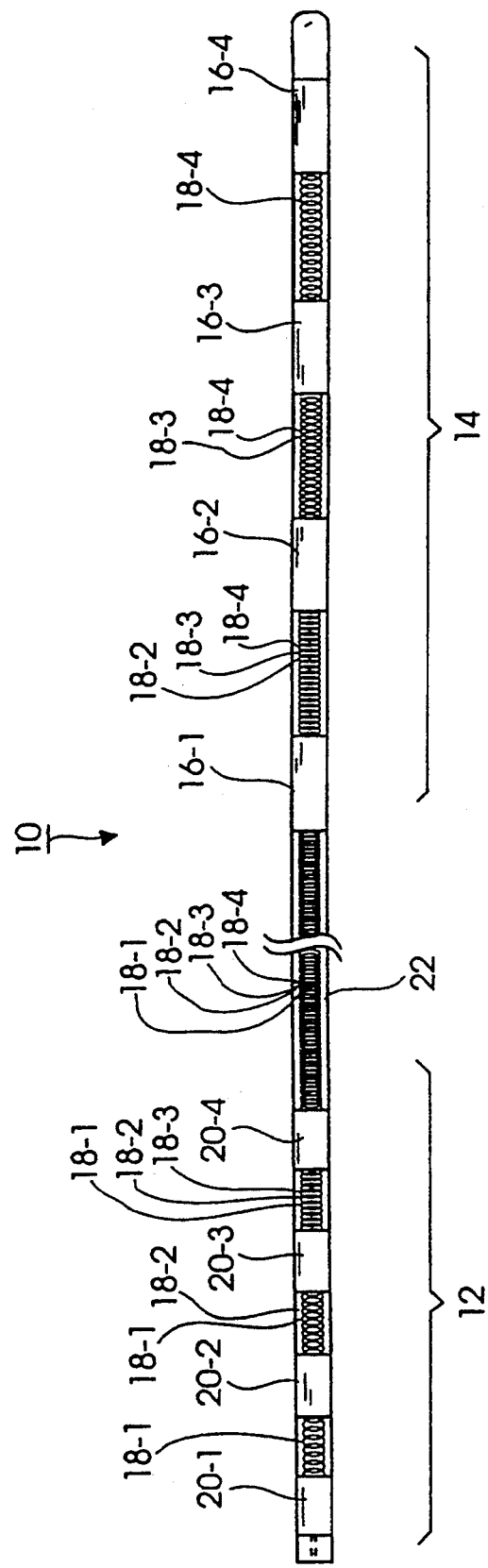
FIG. 5 is an enlarged illustration of an implantable lead.

Referring now to FIG. 5, there is shown a greatly enlarged view of an implantable neurological stimulating lead 10, which may be any one of a number of well-known, commercially available leads such as the Model 3487A available from Medtronic, Inc., Minneapolis, Minn. Although lead 10 is entirely straight in FIG. 5, it will be readily appreciated by those familiar with conventional implantable leads that lead 10 is actually constructed so as to be very flexible. Lead 10 has a proximal or connector end 12 that is adapted to be electrically coupled to an implantable stimulating pulse generator, such as the Medtronic Model 7424. A distal end 14 of lead 10 is adapted to be surgically inserted into the epidural space adjoining the spinal column of a patient.

Distal end 14 of lead 10 has four ring-type electrodes 16-1, 16-2, 16-3, and 16-4 disposed in a spaced-apart relationship on the surface thereof, in accordance with common practice in the art. Electrodes 16-1, 16-2, 16-3, and 16-4 are electrically isolated from one another, and are coupled, via mutually insulated, helically-coiled wire conductors 18-1, 18-2, 18-3, and 18-4, respectively, to respective ring-type electrical contacts 20-1, 20-2, 20-3, and 20-4, disposed on the surface of proximal end 12 of lead 10. Conductors 18-1, 18-2, 18-3, and 18-4 are coaxially coiled, thereby creating a hollow cylindrical lumen along the axis of lead 10, into which a stiffening wire, commonly called a stylet, may be inserted to increase the rigidity of lead 10 during the implant procedure, in accordance with common and well-known practice in the art. The stylet enhances the steerability of lead 10 during implantation, and is withdrawn thereafter to render lead 10 suitably flexible.

Lead 10 is surrounded along its entire length by a flexible outer sheath 22, which may be silicone rubber, polyurethane, or other suitable biocompatible material, also in accordance with common practice in the art.

As previously noted, proximal end 12 of lead 10 is adapted to be permanently connected to the connector block of an implantable pulse generator or the like, in a manner commonly known in the art, once lead 10 has been implanted into a desired position in a patient. Due to the extremely small size of lead 10 and in particular the small size of contacts 20-1, 20-2, 20-3, and 20-4 on lead 10, it has been difficult or inconvenient in the prior art to establish temporary connections to electrodes 20-1, 20-2, 20-3, and 20-4 for the purposes of testing the placement of lead 10 during the implant procedure.

Thus, in accordance with the presently disclosed embodiment of the invention, a stylet 40 having a special end piece 42 is provided, as shown in FIGS. 6a and 6b. End piece 42 is provided with a one or more grooves 44 therein, allowing one end of stylet 40 to be bent and secured therein, either frictionally, or by gluing, thermal bonding, or the like. As shown in FIGS. 6a and 6b, a bend near one end of stylet 40 keeps stylet 40 from being pulled axially out of end piece 42. End piece 42 has a series of notches 46 cut therein, with the portions between notches 46 having a longitudinal groove 48 therein.

Figure 7A:
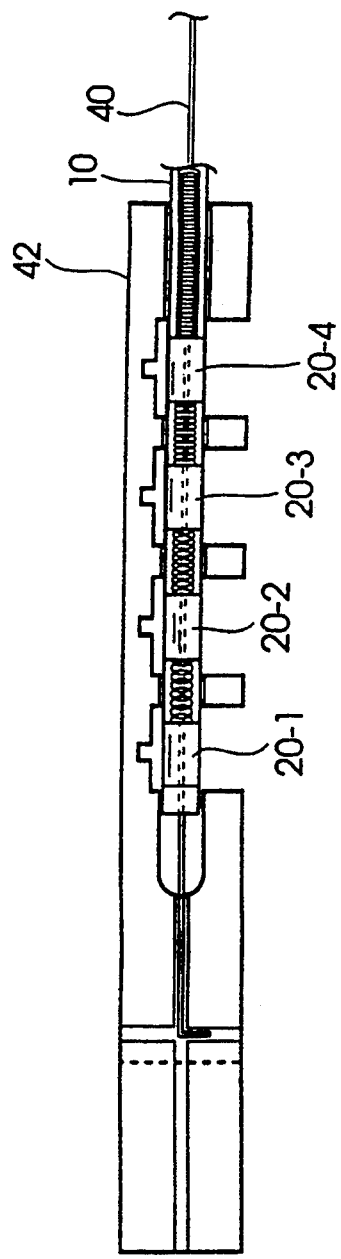
FIGS. 7a and 7b are top and side views, respectively, of the stylet and end piece from FIGS. 6a and 6b with the stylet from FIGS. 6a and 6b inserted into the center of the lead from FIG. 5.
Figure 7B:
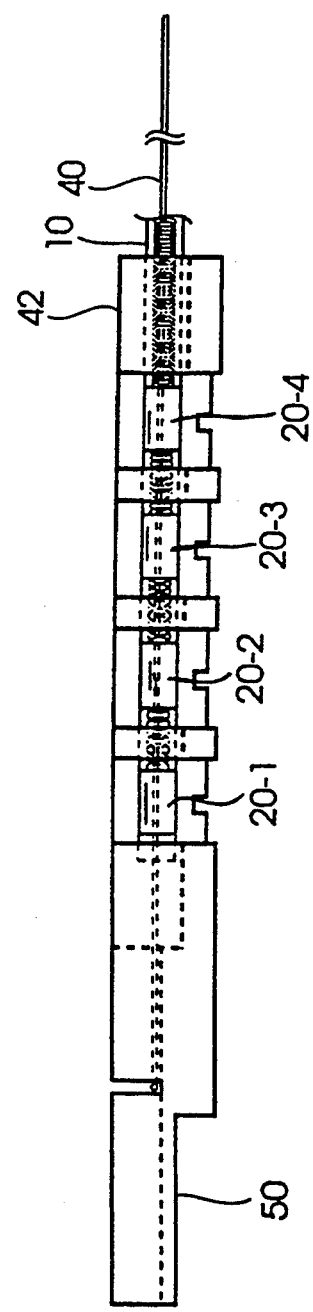

Turning now to FIGS. 7a and 7b, stylet 40 and end piece 42 are shown after stylet 40 has been inserted longitudinally into the lumen at the proximal end 12 of lead 10. As can be seen in FIGS. 7a and 7b, proximal end 12 of lead 10 fits into longitudinal groove 48 in end piece 42. Proximal end 12 of lead 10 is supported and frictionally gripped within in groove 48, yet electrodes 20-1, 20-2, 20-3, and 20-4 remain exposed in notches 46.

Once stylet 40 has been inserted into lead 10 as shown in FIGS. 7a and 7b, distal end 12 of lead 10 can then be received in slots 9-1 and 9-2 in connector 4, when connector 4 is in the 'open' position such that slots 9-1 and 9-2 are brought into alignment. The process of inserting end piece 42, with lead 10 fitted therein, into connector 4 is depicted in FIGS. 8a, 8b, 8c, and 8d.

Figure 8A:
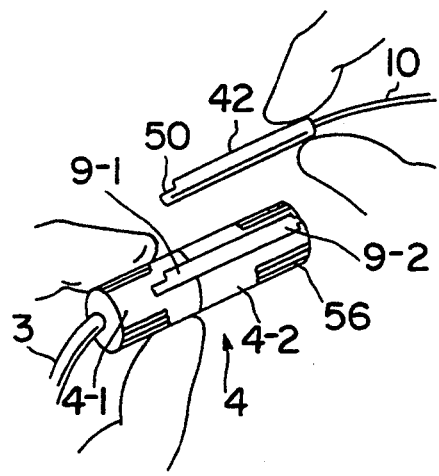
FIGS. 8a, 8b, 8c, and 8d illustrate various stages in the process of connecting the lead from FIG. 5 with the connector from FIGS. 1 through 3.
Figure 8B:
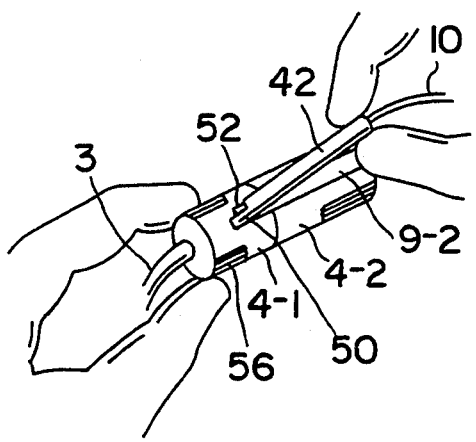
Figure 8C:
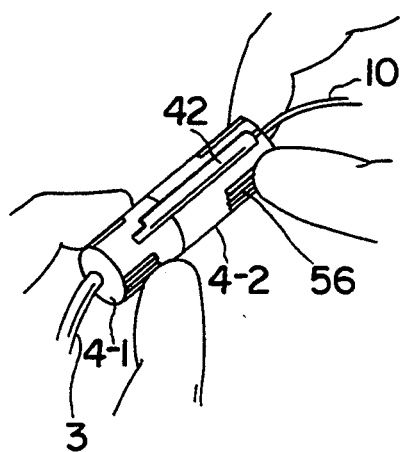

Referring to FIG. 8a, end piece 42 is oriented over slots 9-1 and 9-2 such that a keyed corner 50 thereof is aligned with a corresponding keyed corner 52 in notch 9-1. As would be appreciated by those of ordinary skill in the art, the provision of keyed corners 50 and 52 permits end piece 42 to be inserted in only one way into slots 9-1 and 9-2. As shown in FIG. 8b, end piece 42 is then lowered into slots 9-1 and 9-2. After this is done, end piece 42 rests within grooves 9-1 and 9-2 so that ring-type contacts 20-1, 20-2, 20-3, and 20-4 are brought into contact with correspondingly spaced contacts 7-1, 7-2, 7-3, and 7-4 in connector 4. Lead 10 extends out the end of connector half 4-2 through groove 34 in the end thereof, previously described with reference to FIG. 4.

Figure 8D:
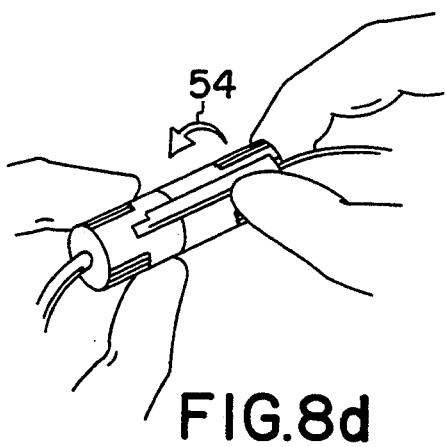
Figure 9:
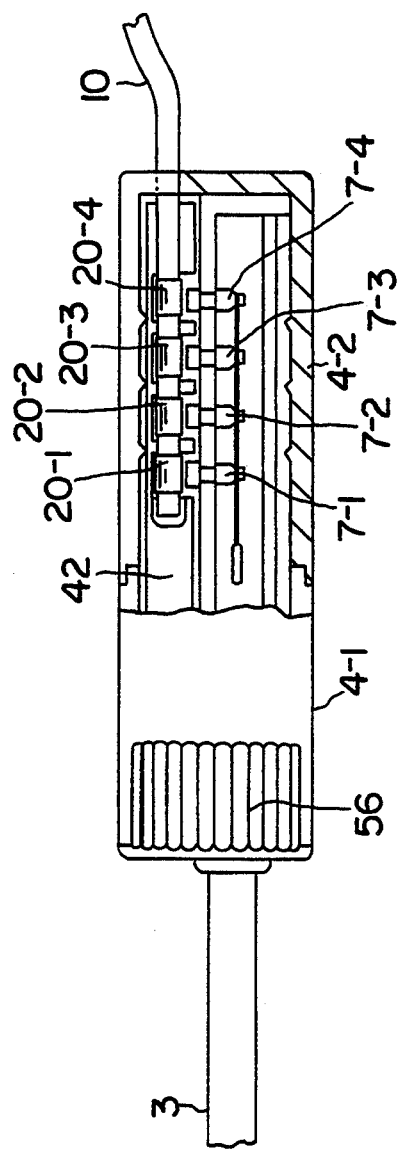
FIG. 9 is an enlarged, partially cut-away illustration of the connector from FIGS. 1 through 3 having the lead, stylet and end piece from FIGS. 7a and 7b inserted therein.

The final stage of the connection process is the twisting closure of connector 4 that is depicted in FIG. 8d. Closing connector 4 involves twisting connector half 4-2 in the direction of arrow 54 while holding connector half 4-1 in place. In so doing, slot 9-2 in connector half 4-2 is brought out of alignment with slot 9-1 in connector half 4-1. This prevents end piece 42 from being removed from connector 4, and holds contacts 20-1, 20-2, 20-3, and 20-4 on proximal end 12 of lead 10 against contacts 7-1, 7-2, 7-3, and 7-4 in connector 4. In FIG. 9, a partially cut-away side view of connector 4 with end piece 42 and lead 10 therein is shown after connector 4 has been closed. As can be seen in FIG. 9, notches 46 in end piece 42 allow contacts 20-1, 20-2, 20-3, and 20-4 to be held in contact with contacts 7-1, 7-2, 7-3, and 7-4 in connector 4.

As is apparent from FIGS. 1, 2, 3, 4, and 8a–8d, connector halves 4-1 and 4-2 are provided with longitudinal ridged or otherwise textured areas 56 which facilitate the gripping of the respective connector halves 4-1 and 4-2 during the twisting closure of connector 4.

From the foregoing detailed description of a specific embodiment of the invention, it should be apparent that a connector for electrically coupling an implantable lead to another cable has been disclosed. Although a particular embodiment of the invention has been disclosed herein in detail, this has been done for the purposes of illustration only, and is not intended to be limiting with respect to the scope of the appended claims, which follow. In particular, it is contemplated by the inventors that various substitutions, alterations, and modifications may be made to the embodiment of the invention described herein without departing from the spirit and scope of the invention as defined by the claims. For instance, and has been previously noted herein, while the disclosed embodiment involved a four-electrode, four-conductor lead and connector system, it is believed that it would be a matter of routine for a person of ordinary skill in the art to adapt the disclosed embodiment to support more or less electrodes and conductors.

What is claimed is:

1. A connector for coupling an implantable lead having a plurality of spaced-apart electrical lead contacts disposed on its proximal end to a multiple-conductor cable, said connector comprising:

a first, substantially cylindrical connector half, adapted to be disposed at a first end of the multiple-conductor cable, said first connector half having a first longitudinal slot therein;

a second, substantially cylindrical connector half, coaxially coupled to said first connector half and axially rotatable with respect to said first connector half from a first, open position to a second, closed position, said second connector half having a second longitudinal slot therein, said second longitudinal slot being aligned with said first longitudinal slot when said second connector half is rotated to said open position;

a plurality of spaced-apart electrical contacts disposed within said first connector half, each one of said plurality of electrical contacts being adapted to be electrically coupled to a conductor in said multiple-conductor cable, said plurality of spaced-apart electrical contacts being exposed in said second slot when said second connector half is rotated to said open position;

an end piece disposed in said first and second longitudinal slots when said second connector half is in said open position, said end piece being adapted to engage the proximal end of the lead such that the plurality of spaced-apart electrical lead contacts are at least partially exposed, the connector being further adapted to permit said second connector half to be rotated into said closed position over said end piece, such that each one of the plurality of spaced-apart electrical lead contacts is held in contact with a respective one of said plurality of spaced-apart electrical contacts in the connector.

2. A connector in accordance with claim 1, further comprising:
   a lead stylet, coupled to said end piece such that said stylet extends into an axial lumen in said lead when said end piece engages said proximal end of said lead.

3. A connector in accordance with claim 1, wherein said end piece is keyed with respect to said first and second longitudinal slots such that said end piece is permitted to be received in said first and second longitudinal slots in only one orientation.

4. A connector in accordance with claim 1, further comprising:
   a locking means for releasably locking the connector in one of the open position and the closed position.

5. A connector in accordance with claim 4 wherein said locking means comprises a plurality of longitudinal grooves in one of said connector halves and at least one raised portion on the other of said connector halves, said at least one raised portion being located to mate with at least one of said grooves when the connector is in the open position and to mate with at least one of said grooves when the connector is in the closed position.

* * * * *